US009978528B2

(12) United States Patent
Hahl et al.

(10) Patent No.: US 9,978,528 B2
(45) Date of Patent: May 22, 2018

(54) HIGH VOLTAGE CAPACITOR HAVING A DUAL TANTALUM ANODE/CATHODE CURRENT COLLECTOR ELECTRODE ASSEMBLY HOUSED IN A DUAL SEPARATOR ENVELOPE DESIGN

(71) Applicant: Greatbatch Ltd., Clarence, NY (US)

(72) Inventors: Jason T. Hahl, East Aurora, NY (US); Barry C. Muffoletto, Alden, NY (US); Todd C. Sutay, Warsaw, NY (US); Glenn A. Dumais, East Aurora, NY (US); Wendy J. Baumler, Akron, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days. days.

(21) Appl. No.: 15/356,727

(22) Filed: Nov. 21, 2016

(65) Prior Publication Data

US 2017/0148576 A1    May 25, 2017

Related U.S. Application Data

(60) Provisional application No. 62/258,130, filed on Nov. 20, 2015.

(51) Int. Cl.
*H01G 9/02* (2006.01)
*H01G 9/042* (2006.01)
(Continued)

(52) U.S. Cl.
CPC ............ *H01G 9/042* (2013.01); *A61N 1/375* (2013.01); *A61N 1/3968* (2013.01); *H01G 9/008* (2013.01);
(Continued)

(58) Field of Classification Search
CPC ...................................................... H01G 9/02
See application file for complete search history.

(56) References Cited

U.S. PATENT DOCUMENTS

| 5,894,403 A | 4/1999 | Shah et al. |
| 5,920,455 A | 7/1999 | Shah et al. |

(Continued)

OTHER PUBLICATIONS

Extended European Search, Application 16199885.1, dated Jan. 30, 2017.

*Primary Examiner* — Eric Thomas
(74) *Attorney, Agent, or Firm* — Michael F. Scalise

(57) ABSTRACT

A capacitor having at least two side-by-side anodes with a cathode current collector disposed between the anodes and housed inside a casing is described. Cathode active material is supported on the opposed major faces of the current collector and the current collector/cathode active material subassembly is housed in a first separator envelope. The first separator envelope is positioned between the side-by-side anodes and this electrode assembly is then contained in a second separator envelope. The two anodes can be connected in parallel inside or outside casing, or they can be unconnected to each other. There is also cathode active material supported on inner surfaces of the casing in a face-to-face alignment with an adjacent one of the anodes. That way, the second separator envelope also prevents direct physical contact between the anode pellets and the cathode active material supported on the casing sidewalls.

21 Claims, 7 Drawing Sheets

(51) Int. Cl.
    *H01G 9/10*     (2006.01)
    *H01G 9/052*    (2006.01)
    *H01G 9/008*    (2006.01)
    *H01G 9/00*     (2006.01)
    *A61N 1/375*    (2006.01)
    *A61N 1/39*     (2006.01)
    *H01G 9/06*     (2006.01)
    *H01G 9/12*     (2006.01)
    *H01G 9/14*     (2006.01)
    *H01G 9/04*         (2006.01)

(52) U.S. Cl.
    CPC ............ *H01G 9/0029* (2013.01); *H01G 9/02* (2013.01); *H01G 9/0425* (2013.01); *H01G 9/052* (2013.01); *H01G 9/06* (2013.01); *H01G 9/10* (2013.01); *H01G 9/12* (2013.01); *H01G 9/14* (2013.01); *H01G 2009/05* (2013.01)

(56)            References Cited

U.S. PATENT DOCUMENTS

| | | | |
|---|---|---|---|
| 5,926,362 A | 7/1999 | Muffoletto et al. | |
| 6,219,222 B1 | 4/2001 | Shah et al. | |
| 6,224,985 B1 | 5/2001 | Shah et al. | |
| 6,334,879 B1 | 1/2002 | Muffoletto et al. | |
| 6,468,605 B2 | 10/2002 | Shah et al. | |
| 6,687,117 B2 | 2/2004 | Liu et al. | |
| 6,819,544 B1 | 11/2004 | Nielsen et al. | |
| 6,850,405 B1 * | 2/2005 | Mileham | A61N 1/375 29/25.41 |
| 7,012,799 B2 | 3/2006 | Muffoletto et al. | |
| 7,072,171 B1 | 7/2006 | Muffoletto et al. | |
| 7,085,126 B2 | 8/2006 | O'Connor et al. | |
| 7,092,242 B1 | 8/2006 | Gloss et al. | |
| 7,116,547 B2 | 10/2006 | Seitz et al. | |
| 7,196,899 B1 | 3/2007 | Feger et al. | |
| 7,348,097 B2 * | 3/2008 | Nielsen | H01G 9/10 174/50 |
| 7,483,260 B2 | 1/2009 | Ziarniak et al. | |
| 7,813,107 B1 | 10/2010 | Druding et al. | |
| 8,027,149 B2 | 9/2011 | Hahl et al. | |
| 8,086,312 B2 | 12/2011 | Norton et al. | |
| 9,312,075 B1 | 4/2016 | Liu et al. | |
| 2003/0017385 A1 | 1/2003 | Frustaci et al. | |
| 2003/0090857 A1 | 5/2003 | Liu et al. | |
| 2006/0061938 A1 | 3/2006 | Dombro et al. | |
| 2008/0068779 A1 * | 3/2008 | Restorff | H01G 9/02 361/508 |
| 2011/0026188 A1 * | 2/2011 | Nielsen | A61N 1/375 361/500 |

* cited by examiner

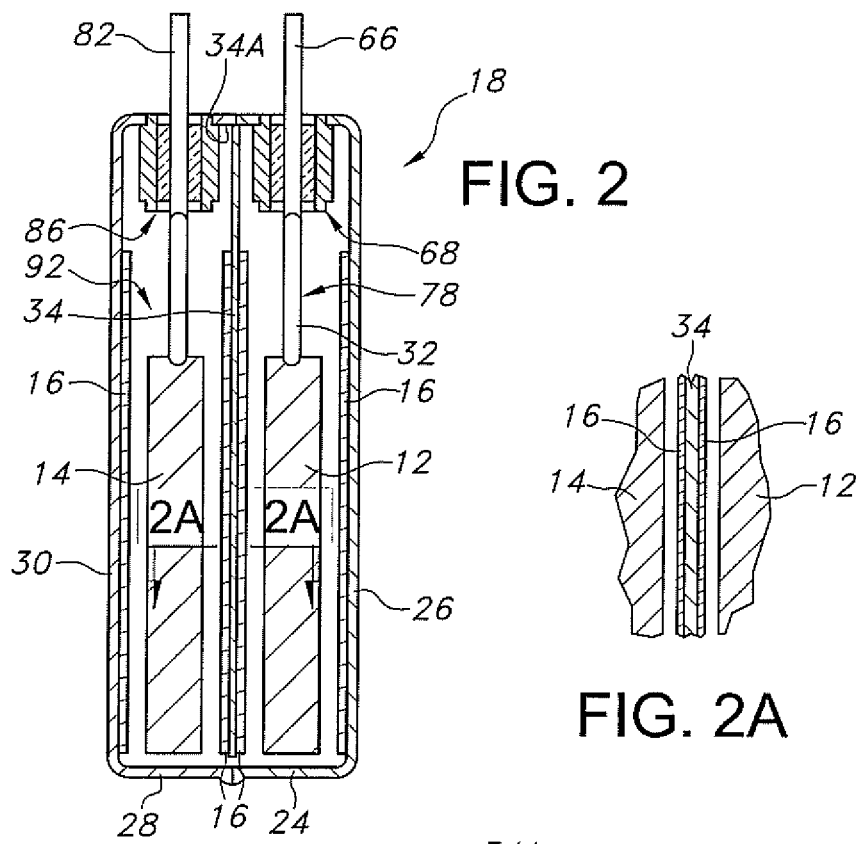
FIG. 2
FIG. 2A
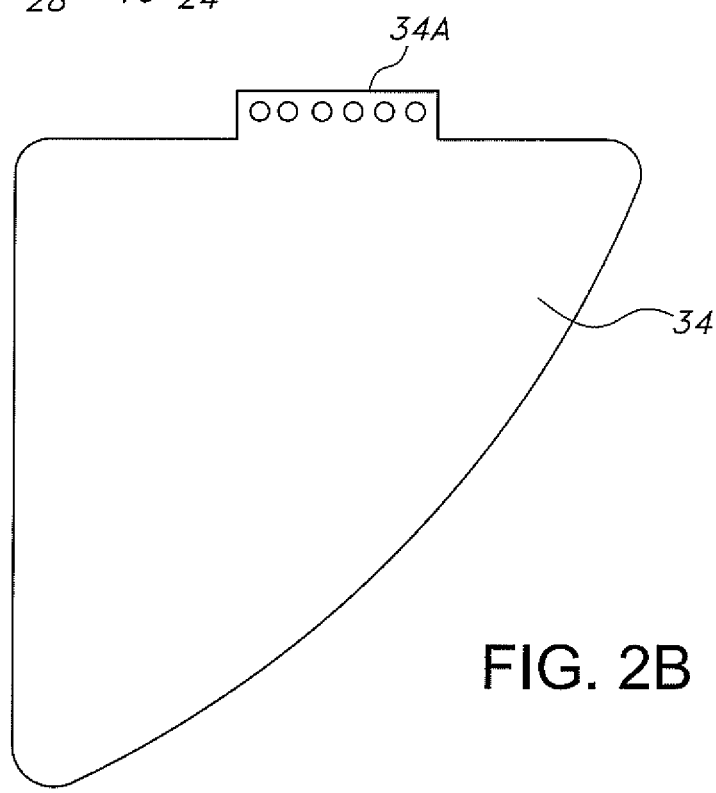
FIG. 2B

HIGH VOLTAGE CAPACITOR HAVING A DUAL TANTALUM ANODE/CATHODE CURRENT COLLECTOR ELECTRODE ASSEMBLY HOUSED IN A DUAL SEPARATOR ENVELOPE DESIGN

CROSS-REFERENCE TO RELATED APPLICATION

This application claims priority to U.S. provisional patent application Ser. No. 62/258,130, filed on Nov. 20, 2015.

BACKGROUND OF THE INVENTION

1. Field of the Invention

The present invention generally relates to a capacitor, and more particularly, to a capacitor having a cathode of an active material supported on a casing sidewall and on an intermediate current collector disposed between two spaced apart side-by-side anode pellets. The intermediate current collector/cathode active material subassembly is housed in a first separator envelope, which is positioned between the side-by-side anodes to form an electrode assembly. This electrode assembly is then housed in a second separator envelope. That way, the anode and cathode are kept from direct physical contact with each other by the "bag-in-a-bag" separator design of the present invention. A working electrolyte filled into the casing serves as an ionic transport for charging and discharging the capacitor.

2. Prior Art

U.S. Pat. No. 7,483,260 to Ziarniak et al., which is assigned to the assignee of the present invention and incorporated herein by reference, describes a capacitor having side-by-side first and second anodes electrically connected in parallel to each other inside a casing. The anodes are housed in their own separator envelopes; however, heat sealing each anode in its own envelope is complicated. It is particularly difficult to seal and trim the second separator envelope without damaging the first envelope.

Thus, while the prior art separator design functions well for preventing contact between the anode and cathode active materials in a dual anode capacitor, there is a need for an alternate design.

SUMMARY OF THE INVENTION

The present invention is directed to a capacitor having at least two side-by-side anodes, each preferably in the form of a tantalum pellet, housed inside a casing. An exemplary casing includes two shallow-drawn casing portions, each housing one of the anode pellets and each in the shape of a clamshell having their annular rims butt welded each other. A cathode current collector is disposed between the two anode pellets. Cathode active material is supported on the opposed major faces of the current collector and the current collector/cathode active material subassembly is housed in a first separator envelope. The first separator envelope housing the cathode current collector/cathode active material subassembly is positioned between side-by-side anodes and this electrode assembly is then contained in a second separator envelope. The two anodes can be connected in parallel inside or outside the casing, or they can be left unconnected to each other.

In most dual anode designs there is also cathode active material supported on inner surfaces of the casing in a face-to-face alignment with an adjacent one of the anodes. That way, the second separator envelope also prevents direct physical contact between the anode pellets and the cathode active material supported on the casing sidewalls. With the casing serving as the cathode terminal, the first and second separator envelopes prevent short circuit contact of the anode with the cathode or with the cathode terminal.

These and other objects of the present invention will become increasingly more apparent to those skilled in the art by reference to the following detailed description and the appended drawings.

BRIEF DESCRIPTION OF THE DRAWINGS

FIG. 2 is a cross-sectional view of the capacitor 10 illustrated in FIG. 1.

FIG. 2A is a cross-sectional view along line 2A-2A of FIG. 2.

FIG. 2B is a side elevational view of a cathode current collector 34 before it is incorporated into the capacitor 10 illustrated in FIG. 1.

Figure 1:
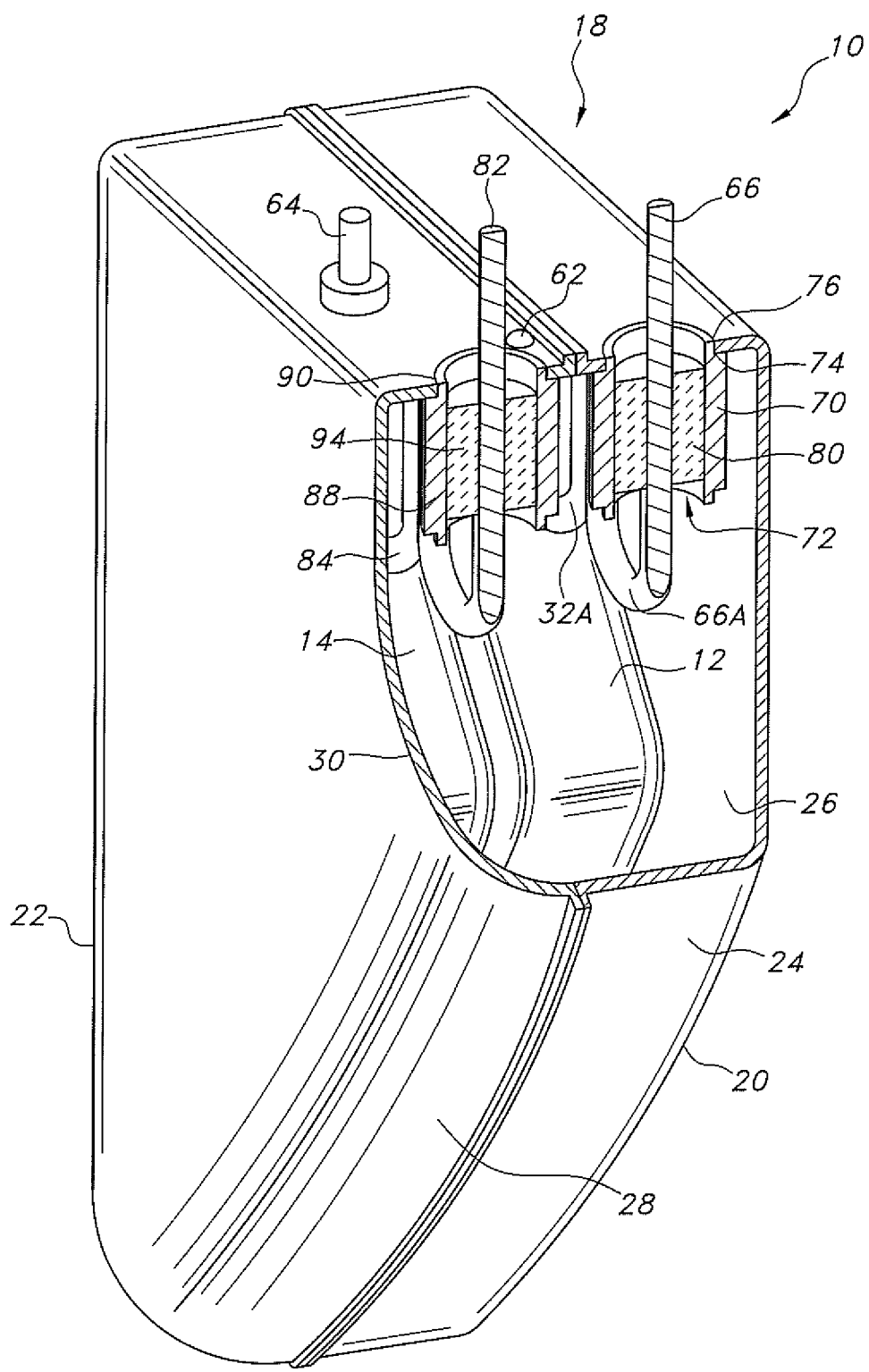
FIG. 1 is a perspective view looking at the left edge of a dual anode capacitor 10 according to one embodiment of the present invention.

The present invention will be described in connection with preferred embodiments, however, it will be understood that there is no intention to limit the invention to the embodiments described. On the contrary, the intent is to cover all alternatives, modifications, and equivalents as may be included within the spirit and scope of the invention as defined by the appended claims.

DETAILED DESCRIPTION OF THE PREFERRED EMBODIMENTS

Referring now to the drawings, FIGS. 1, 2, 2A, 2B, 3 and 4 illustrate an exemplary capacitor 10 that is useful with the various separator designs (FIGS. 5 to 7) according to the present invention. As will be described in detail hereinafter, capacitor 10 is well suited for implantable cardiac device capacitor applications.

Capacitor 10 comprises a first anode 12 of a first anode active material, a second anode 14 of a second anode active material, and a cathode of a cathode active material 16 (FIGS. 2A and 5 to 7) housed inside a hermetically sealed casing 18. Preferably, the side-by-side first and second anodes 12, 14 are of the same active material. The capacitor 10 can be of either an electrochemical type wherein the anode and the cathode are provided by conductive substrates having a capacitive material contacted thereto or, an electrolytic type wherein the cathode is provided by a conductive substrate having capacitive properties where the anode is of a valve metal. The illustrated capacitor 10 is preferably of the latter type, however, that should not be construed as limiting. The capacitor electrodes are operatively associated with each other by an electrolyte (not shown) contained inside the casing 18.

Exemplary casing 18 is of metal material comprising first and second clamshell portions 20 and 22. Casing portion 20 comprises a surrounding sidewall 24 extending to a face wall 26. Similarly, casing portion 22 comprises a surrounding sidewall 28 extending to a face wall 30. The sidewalls 24 and 28 are sized to butt up to each other. Then, the casing portions 20, 22 are hermetically sealed together by welding the sidewalls 24, 28 where they contact. The weld is provided by any conventional means; however, a preferred method is by laser welding.

The casing clamshells 20, 22 are made of a conductive metal selected from the group consisting of tantalum, titanium, nickel, niobium, stainless steel, aluminum, zirconium, and mixtures thereof. Regardless the metal, the clamshells 20, 22 have a thickness of about 0.015 to about 0.5 millimeters and serve as one terminal or contact for making electrical connection between the capacitor and its load.

The active material of the anodes 12 and 14 is typically of a metal in the form of a pellet. The anode metal is selected from the group of valve metals consisting of tantalum, aluminum, titanium, niobium, zirconium, hafnium, silicon, and mixtures thereof. As is well known by those skilled in the art, the anode metal in powdered form, for example tantalum powder, is compressed into a pellet having an anode lead (lead 32 for anode 12 and lead 84 for anode 14) embedded therein and extending there from, and sintered under a vacuum at high temperatures. The porous body is then anodized in a suitable electrolyte to fill its pores with the electrolyte and form a continuous dielectric oxide film on the sintered body. A preferred tantalum material and method of manufacturing an anode pellet for the present capacitor 10 is described in U.S. Pat. No. 9,312,075 to Liu et al., which is assigned to the assignee of the present invention and incorporated herein by reference.

In particular, the anode pellets 12, 14 and their leads 32, 84 are anodized by immersing the assembly in an electrolyte and applying a current. The electrolyte includes constituents such as water and phosphoric acid and perhaps other organic solvents. The application of current drives the formation of an oxide film that is proportional in thickness to the targeted forming voltage. A pulsed formation process may be used wherein current is cyclically applied and removed to allow diffusion of heated electrolyte from the internal pores of the anodes. Intermediate washing and annealing steps may be performed to facilitate the formation of a stable, defect free oxide. Preferably, the anode pellets 12, 14 and extending leads 32, 84 are anodized to a formation voltage that is greater than zero up to 550 V.

The anode leads 32, 84 preferably comprise the same material as the anodes 12, 14. The anodes 12, 14 can also be of an etched aluminum or tantalum foil.

Cathode active material 16 having a thickness of about a few hundred Angstroms to about 0.1 millimeters is directly coated on the inner surface of the clamshell face walls 26, 30 or, the cathode active material is coated on a conductive substrate (not shown) in electrical contact with the inner surface of the face walls, spaced from the respective sidewalls 24, 28. Another portion of the cathode active material 16 is positioned intermediate the anodes 12, 14. This intermediate cathode active material 16 is supported on the opposed inner surfaces of a current collector 34 (FIGS. 2 and 2A), preferably in the form of a foil.

In that respect, the face walls 26, 30 and the current collector 34 may be of an anodized-etched conductive material, have a sintered active material with or without oxide contacted thereto, be contacted with a double layer capacitive material, for example a finely divided carbonaceous material such as graphite, carbon, activated carbon, platinum black, a redox, pseudocapacitive or an under potential material, or be an electroactive conducting polymer such as polyaniline, polypyrole, polythiophene, and polyacetylene, and mixtures thereof. Preferably, the cathode active material 16 is substantially aligned in a face-to-face, but spaced apart relationship with the major faces of the anodes 12, 14.

According to one preferred aspect of the present invention, the redox or cathode active material 16 includes an oxide of a first metal, the nitride of the first metal, the carbon nitride of the first metal, and/or the carbide of the first metal, the oxide, nitride, carbon nitride and carbide having pseudocapacitive properties. The first metal is preferably selected from the group consisting of ruthenium, cobalt, manganese, tantalum, iron, niobium, iridium, titanium, zirconium, hafnium, rhodium, vanadium, osmium, palladium, platinum, nickel, and lead.

The cathode active material 16 may also include a second or more metals. The second metal is in the form of an oxide, a nitride, a carbon nitride or carbide, and is not essential to the intended use of the conductive face walls 26, 30 and the intermediate current collector 34 as a capacitor electrode. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium. In a preferred embodiment of the invention, the cathode active material 16 includes an oxide of ruthenium and is substantially devoid of the second or more metals.

The cathode active material 16 may also be selected from graphitic or glassy carbon on titanium carbide, carbon and silver vanadium oxide on titanium carbide, carbon and crystalline manganese dioxide on titanium carbide, platinum on titanium, ruthenium on titanium, barium titanate on titanium, carbon and crystalline ruthenium oxide on titanium carbide, carbon and crystalline iridium oxide on titanium carbide, silver vanadium oxide on titanium, and activated carbon.

As disclosed in U.S. Pat. No. 7,116,547 to Seitz et al., a preferred cathode material coating process is by pad printing. This patent is assigned to the assignee of the present invention and incorporated herein by reference. An ultrasonically generated aerosol, as described in U.S. Pat. Nos. 5,894,403, 5,920,455, 6,224,985, and 6,468,605, all to Shah et al., is also suitable for making a coating of the cathode active material 16. These patents and the Seitz et al. patent are assigned to the assignee of the present invention and incorporated herein by reference. In that manner, the ultrasonically generated cathode active material contacted to the conductive surfaces of the clamshell face walls 26, 30 and current collector 34 has a majority of its particles with diameters of less than about 10 microns. This provides an internal surface area for the active material of about 10 m²/gram to about 1,500 m²/gram.

A tab 34A (FIG. 2B) provides for tack welding the current collector 34 to the inner surface of the surrounding sidewall of one of the clamshells 20, 22, for example the surrounding sidewall 28 of clamshell casing portion 22. The current collector 34 is then bent relative to the tab 34A to position it intermediate the anodes 12, 14.

Figure 5:
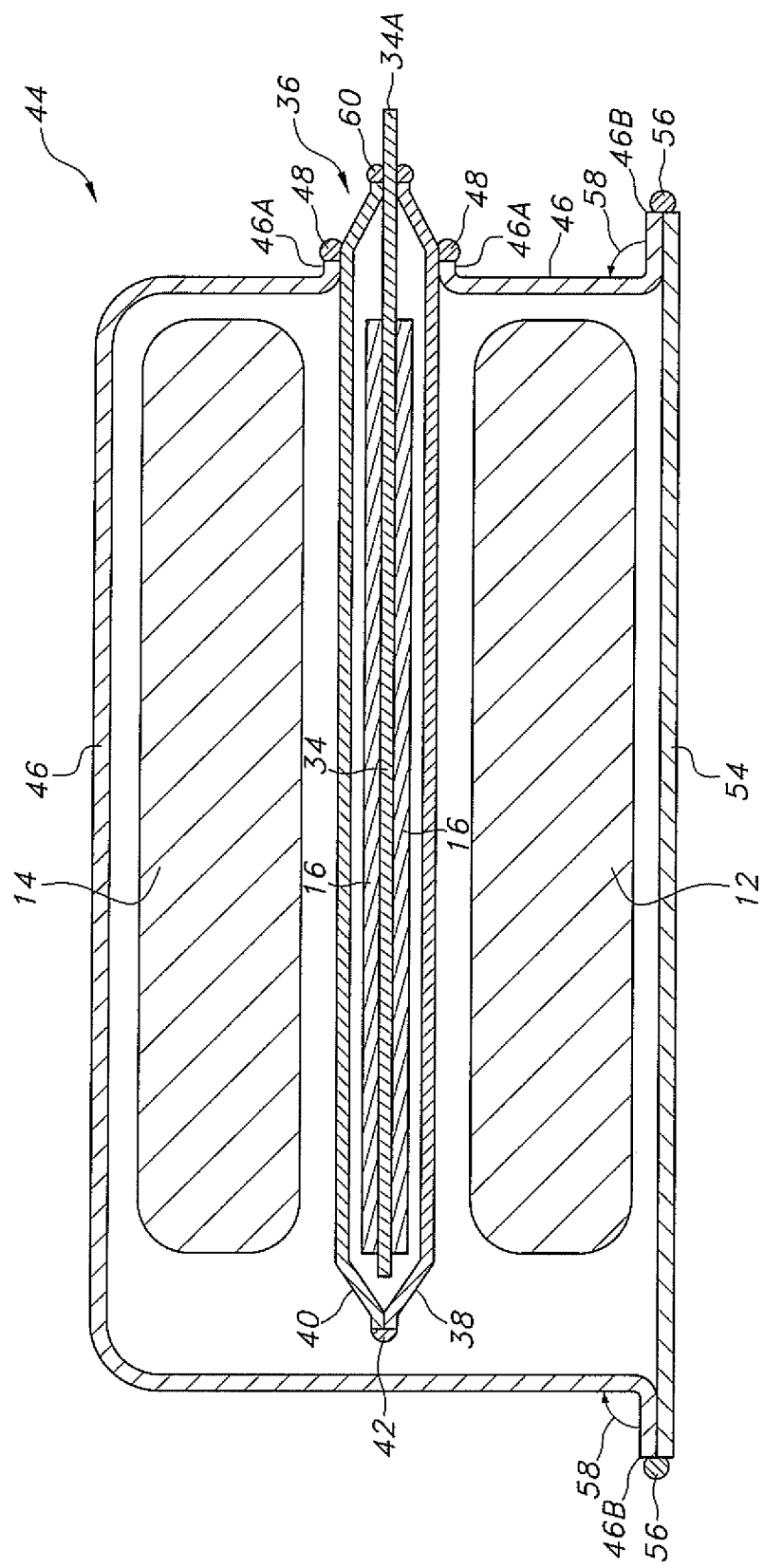
FIG. 5 is a schematic view of an exemplary bag-in-a-bag separator design according to the present invention comprising a first separator envelope 36 for the cathode current collector 34 and a second separator envelope 44 for the anodes 12, 14/cathode active material 16 electrode assembly.

As shown in FIG. 5, to prevent an internal electrical short circuit between the electrodes, a first separator envelope 36 of electrically insulative separator material is provided between the anodes 12 and 14 and the current collector 34 supporting the cathode active material 16. The first envelope 36 comprises opposed first and second sheets 38 and 40 of separator material that are sized and shaped to surround the cathode current collector 34. The sheets 38, 40 are connected to each other at their coincident peripheral margins by any suitable means including adhesive or a heat seal 42.

After the first separator envelope 36 containing the current collector 34/cathode active material 16 subassembly is positioned between the spaced apart anodes 12, 14, a second separator envelope 44 is provided. The second envelope 44 contains or houses the entire electrode assembly comprising the current collector 34/cathode active material 16 subassembly housed in the first envelope 36 and the first and second anodes 12, 14. The second envelope 44 comprises a third separator sheet 46 that is sized and shaped to partially surround the first and second anodes 12, 14. An opening in sheet 46 provides a margin 46A that is secured to the second separator sheet 40 by an adhesive or heat seal 48 provided adjacent to the current collector tab 34A. A distal edge of the third sheet 46 forms an outwardly extending margin 46B.

A fourth separator sheet 54 is sized and shaped to extend to the margin 46B of the third sheet 46. This connection or securement of the fourth separator sheet 54 to the margin 46B of the third sheet 46 is preferably by heat seal. The resulting "bag-in-a-bag" separator construction contains the cathode current collector 34/cathode active material 16 subassembly housed in the first separator envelope 36 and disposed between or intermediate the first and second anodes 12, 14 to form an electrode assembly that is in turn housed in the second separator envelope 44. As depicted by arrows 58, before being positioned inside the casing 18, the margin 46B and meeting fourth separator sheet 54 are folded against the main body of the respective third 46.

As previously described, the current collector tab 34A extends outwardly from the first separator envelope 36 for connection to a cathode terminal, for example for connection to an inner surface of one of the casing clamshells 20, 22. An adhesive material or heat seal 60 secures the first and second separator sheets 38, 40 to the cathode current collector 34 at this location.

The respective separator sheets 38, 40, 46 and 54 are of materials that are chemically unreactive with the anode and cathode active materials and both chemically unreactive with and insoluble in the electrolyte. In addition, the separator sheets have a degree of porosity sufficient to allow flow therethrough during charging and discharging of the capacitor 10.

Illustrative separator materials include woven and non-woven fabrics of polyolefinic fibers including polypropylene and polyethylene, or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR®, (DMS Solutech); a polytetrafluoroethylene membrane commercially available under the designation ZITEX®, (Chemplast Inc.) or EXCELLERATOR®, (W.L. Gore and Associates); a polypropylene membrane commercially available under the designation CELGARD®, (Celgard LLC); and a membrane commercially available under the designation DEXIGLAS®, (C. H. Dexter, Div., Dexter Corp.). Cellulose based separators also typically used in capacitors are contemplated by the scope of the present invention. Depending on the electrolyte used, the separators 38, 40, 46 and 54 can be treated to improve their wettability, for example with a surfactant, as is well known by those skilled in the art.

A suitable electrolyte for the capacitor 10 is described in U.S. Pat. No. 6,219,222 to Shah et al., which includes a mixed solvent of water and ethylene glycol having an ammonium salt dissolved therein. U.S. Patent Pub. Nos. 2003/0090857 and 2003/0142464 describe other electrolytes for the present capacitors. The electrolyte of the former publication comprises water, a water-soluble inorganic and/or organic acid and/or salt, and a water-soluble nitro-aromatic compound while the latter relates to an electrolyte having de-ionized water, an organic solvent, isobutyric acid and a concentrated ammonium salt. These publications and patent are assigned to the assignee of the present invention and incorporated herein by reference. The electrolyte is provided inside the hermetically sealed casing through a fill opening closed by a hermetic closure 62, as is well known by those skilled in the art.

The casing 18, including the clamshells 20, 22, being of a conductive metal serves as one terminal for making electrical connection between the capacitor 10 and its load. A pin 64 is welded to the clamshell sidewall 24 to provide the negative terminal for the capacitor 10.

As shown in FIGS. 1 and 2, a conductor or feedthrough lead 66 connected to the anode wire 32 extends from the anode 12 housed in the casing 18 and through the first surrounding sidewall 24. The anode feedthrough lead 66 is electrically insulated from the metal casing 18 by an insulator glass-to-metal seal 68. The glass-to-metal seal comprises a ferrule 70 defining an internal through bore or passage 72, preferably, but not necessarily of a constant inside diameter. An annular step 74 provided at the upper end is of an outer diameter sized to fit in a closely spaced relationship in an annular opening 76 in the first clamshell sidewall 24 with the remaining body of the ferrule butted against the inner surface of the sidewall. The ferrule 70 is secured therein by welding, and the like.

Figure 3:
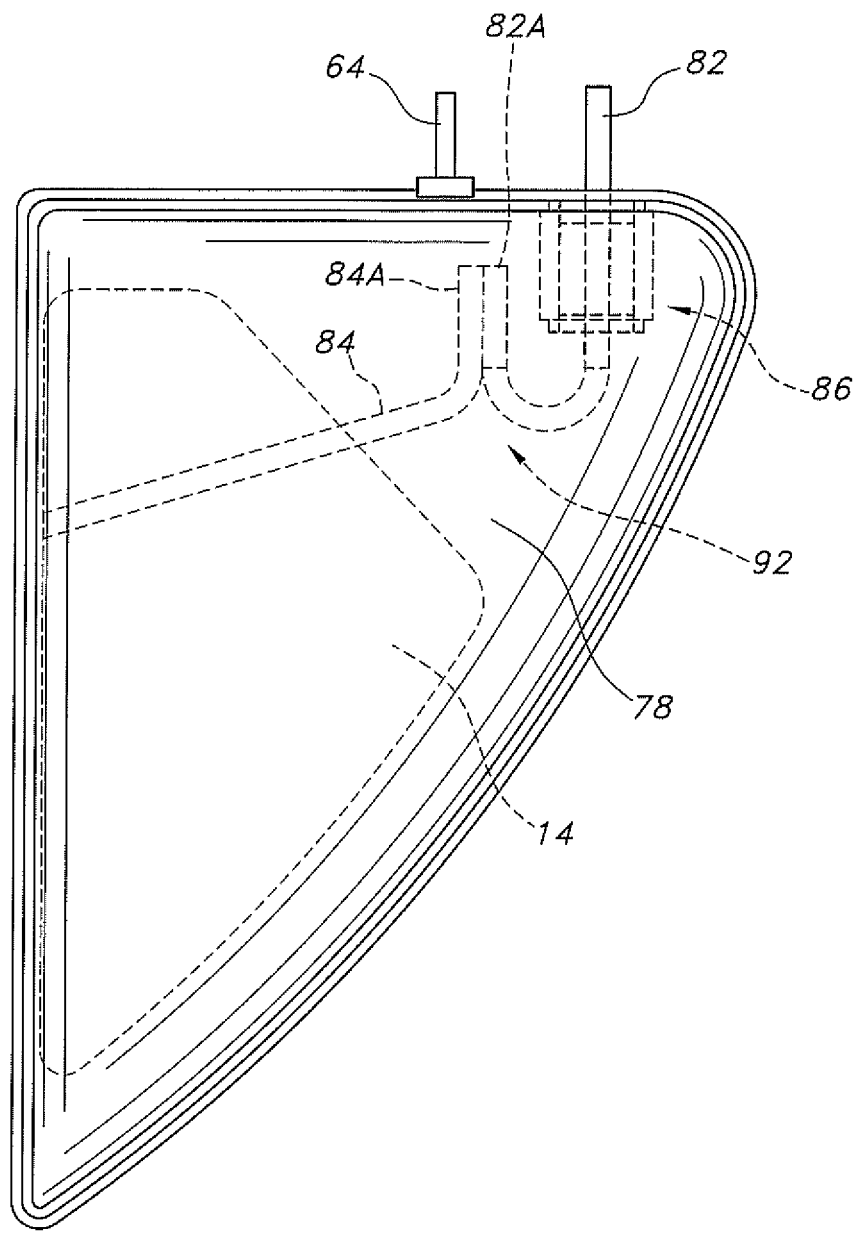
FIG. 3 is a side elevational view, partly in phantom, of the dual anode capacitor 10 of FIG. 1.

As shown in FIGS. 2 and 3, the anode 12 has a notch 78 that provides clearance for the glass-to-metal seal 68. The anode wire 32 embedded in the anode active material extends outwardly from the notch 78 and has a distal end 32A bent into a position generally parallel to the longitudinal axis of ferrule 70. A proximal end 66A of the anode feedthrough lead 66 is bent into a J-hook shape that is aligned substantially parallel to the distal end 32A of the anode wire 32. The distal end 32A of the anode wire is then welded to the proximal end 66A of the feedthrough lead 66.

An insulative glass 80 provides a hermetic seal between the inside of the ferrule 70 and the anode feedthrough lead 66. The glass is, for example, ELAN® type 88 or MANSCL™ type 88. The feedthrough lead 66 preferably comprises the same material as the anode active material. In that manner, the portion of the feedthrough lead 66 extending outside the capacitor 10 is hermetically sealed from the interior of the capacitor and insulated from the mating casing clamshells 20, 22 serving as the terminal for the cathode electrode.

The other anode 14 likewise has a conductor or feedthrough lead 82 connected to an anode wire 84 that extends from the anode and through the second surrounding side wall 28. The feedthrough lead 82 is electrically insulated from the metal casing 18 by a glass-to-metal seal 60 comprising a cylindrically shaped ferrule 88. An upper step of the ferrule 88 fits in a closely spaced relationship in an annular opening 90 in the second casing sidewall 28 with the ferrule butted against the inner surface of the sidewall. The ferrule 88 is secured therein by welding, and the like.

In a similar manner as anode 12, anode 14 has a notch 92 (FIGS. 2 and 3) that provides clearance for the glass-to-metal seal 86. The anode wire 84 embedded in the anode active material extends outwardly from the notch with a distal end 84A bent into a position generally parallel to the longitudinal axis of the ferrule 88. A proximal end 82A of the feedthrough lead 82 is bent into a J-hook shape that is aligned substantially parallel to the distal end 84A of the anode wire 84. Welding then electrically connects the anode wire 84 to the feedthrough lead 82.

An insulative glass 94, similar to glass 80 of the glass-to-metal seal 68 for the anode 12, seals between the inside of the ferrule 88 and the anode feedthrough lead 82. This glass hermetically seals that portion of the feedthrough lead 82 extending outside the capacitor 10 from the capacitor interior, insulated from the mating casing clamshells 20, 22.

Alternatively, members 80, 94 are not glass, but, instead, are a synthetic polymeric material such as an elastomeric material that is capable of sealing between feedthrough leads 66, 82 and the inner surface of the respective ferrules 70, 88. A suitable polymeric material for the layers 80, 94 is, for example Master-Sil 151 made by Master Bond. While such a seal structure using only a synthetic polymeric material is not necessarily hermetic, acceptable isolation of the electrolyte from inside of the casing 18 to the outside thereof is provided by the polymer layers 80, 94.

The capacitor 10 illustrated in FIGS. 1 to 3 has the anode feedthroughs 66, 82 left unconnected to each other. This means that the respective anodes 12, 14 are capable of being charged independently of each other. This could take the form of charging one of the anodes partially or completely to a rated voltage, and then charging the other anode. In other situations, it might be preferred to charge one of the anodes at a rate different than that at which the second anode is charged. For example, a pulse current could charge one of the anodes while the other is by constant power charging. An advantage of separately connecting the anode feedthroughs 66, 82 to an external charging circuit is that the charging or discharging currents can be distributed over the several feedthroughs, which allows smaller, more flexible leads and connections than one lead with an equivalent current carrying capacity.

Figure 4:
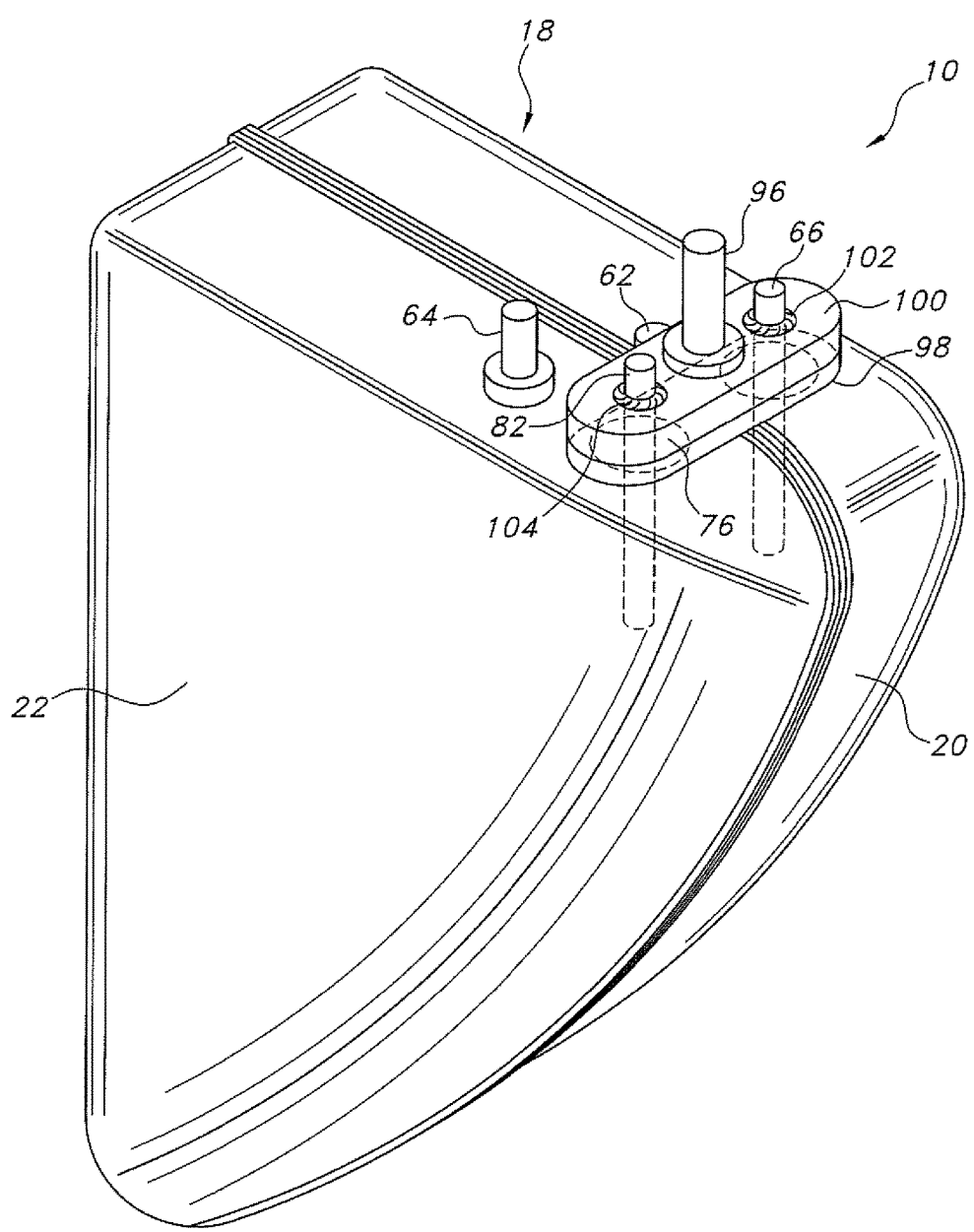
FIG. 4 is a perspective view of the capacitor of FIG. 1 with the anode feedthroughs 66, 82 joined externally of the casing.

As shown in FIG. 4, the anode feedthroughs 66 and 82 for the respective anodes 12, 14 are electrically connected to a common positive polarity terminal 96. This is accomplished by first mounting an insulator 98 having spaced apart openings sized to receive the feedthroughs 66, 82 when resting on the clamshell sidewalls 24, 28. A bridge 100 of a conductive material, for example, nickel, is then supported on the insulator 98. The bridge has a pair of openings that surround the anode feedthroughs 66, 82. The bridge 100 is secured to the feedthroughs 66, 82 by respective welds 102 and 104 to electrically connect them together. Finally, the common positive terminal 96 is electrically connected to bridge 100. The terminal 96 has an enlarged base that is positioned about at the midpoint on the bridge between the feedthroughs 66, 82. In that manner, the terminal 96 is aligned along a common axis with the feedthroughs 66, 82 and electrically secured thereto, such as by welding or soldering. The bridge can also be crimped onto the feedthroughs 66, 82 by applying a force that deforms the bridge from opposed directions onto the feedthroughs.

The capacitor 10 is then connectable to a load (not shown) as a power source. Connecting the negative polarity terminal pin 64 and the common positive terminal 96 does this.

Figure 6:
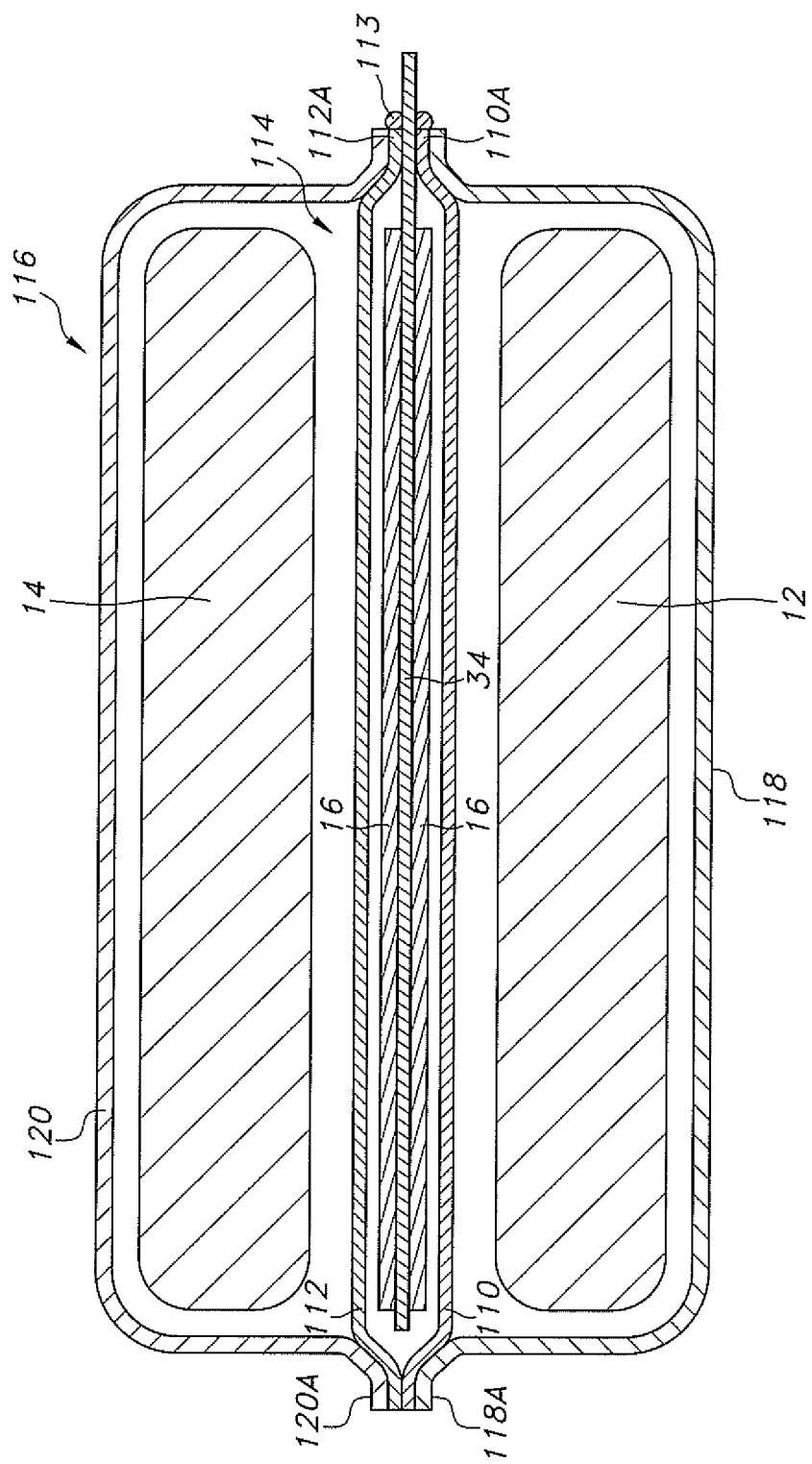
FIG. 6 is a schematic view of another exemplary bag-in-a-bag separator design according to the present invention comprising a first separator envelope 114 for the cathode current collector 34 and a second separator envelope 116 for the anodes 12, 14/cathode active material 16 electrode assembly.

FIG. 6 illustrates another embodiment of a "bag-in-a-bag" separator design for an electrode assembly according to the present invention. This embodiment comprises a fifth and sixth separator sheets 110 and 112 that are sized and shaped to cover respective sides of the current collector 34/cathode active material 16 subassembly. The fifth and sixth separator sheets 110, 112 are connected or secured to each other, for example by an adhesive or heat seal at their coincident peripheral margins 110A, 112A except where the cathode current collector 34 extends outwardly from the sheets 110, 112. There, the margins 110A, 112A are secured to the current collector 34 by a suitable adhesive 113 to thereby contain the cathode current collector 34 in a first separator envelope 114. Alternatively, the margins 110A, 112A are not secured to each other at this time, but, as described presently, will be so secured in a later manufacturing step.

After the first separator envelope 114 containing the intermediate current collector 34/cathode active material 16 subassembly is positioned between the spaced apart anodes 12, 14, a second separator envelope 116 is provided to contain the anodes 12, 14/cathode 16 electrode subassembly. As further shown in FIG. 6, the second envelope 116 comprises seventh and eighth separator sheets 118, 120 that are sized and shaped to house or contain the electrode assembly including the cathode current collector 34 contained in the first separator envelope 114 and positioned between the anode pellets 12, 14. Respective outwardly extending peripheral margins 118A and 120A contact outer surfaces of the margins 110A, 112A of the fifth and sixth sheets 110, 112 of the first envelope 114. This four-ply separator sheet assembly is then sealed together at the coincident overlying margins 110A, 112A, 118A and 120A, for example in a heat seal manufacturing step. Alternatively, an adhesive (not shown) is used to secure the coincident separator margins 110A, 112A, 118A and 120A together.

Figure 7:
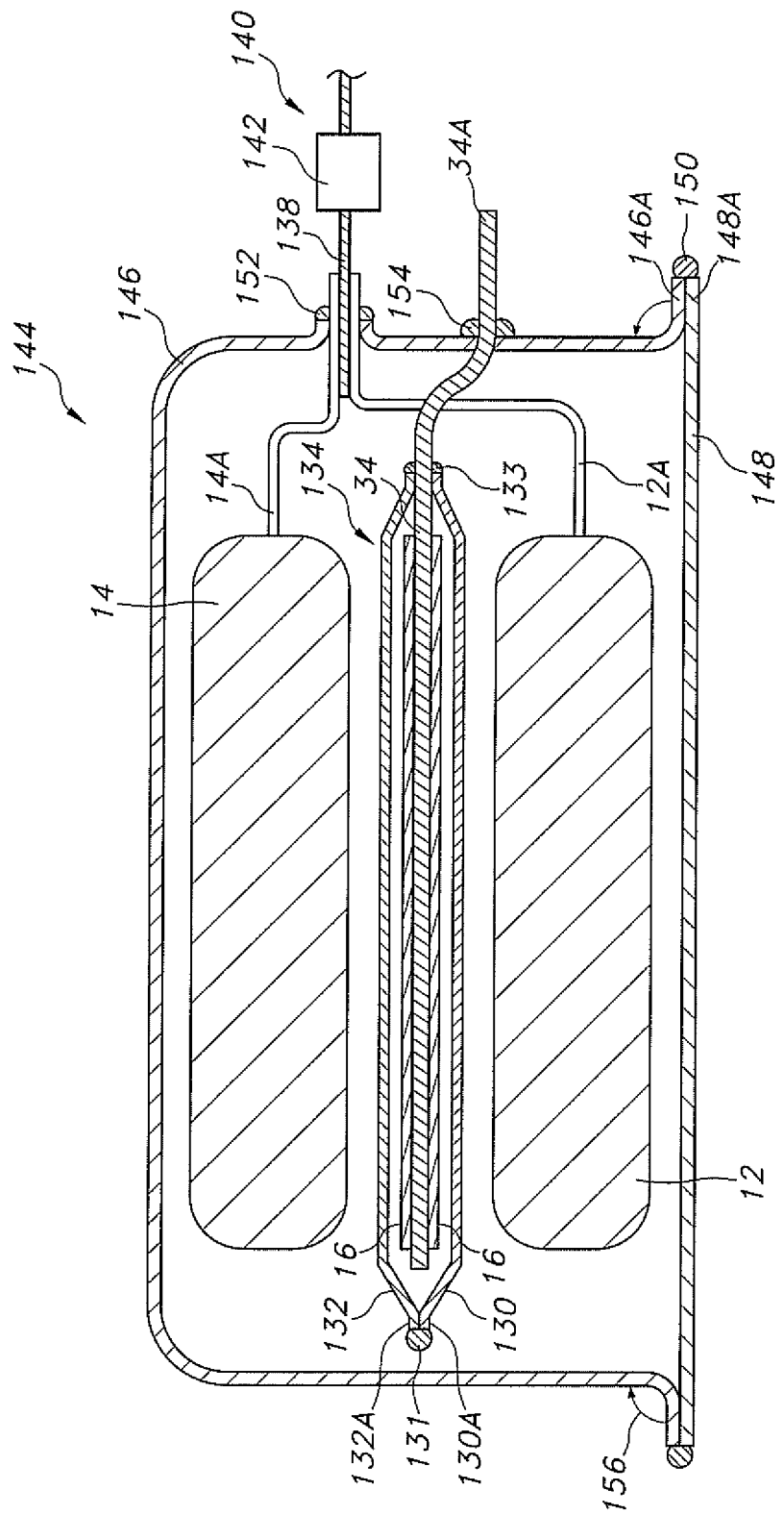
FIG. 7 is a schematic view of another exemplary bag-in-a-bag separator design comprising a first separator envelope 134 for the cathode current collector 34 and a second separator envelope 144 for the anodes 12, 14/cathode active material 16 electrode assembly.

FIG. 7 illustrates another embodiment of a "bag-in-a-bag" separator design for an electrode assembly according to the present invention. This embodiment comprises ninth and tenth separator sheets 130 and 132 that are sized and shaped to cover respective sides of the current collector 34 supporting the cathode active material 16. The ninth and tenth separator sheets 130, 132 have respective outwardly extending peripheral margins 130A, 132A that are secured to each other, for example by an adhesive or heat seal 131 except where the cathode current collector 34 extends outwardly from the sheets 130, 132. There, the margins 130A, 132A are secured to the current collector 34 by a suitable adhesive 133 to thereby form a first separator envelope 134 containing the current collector 34/cathode active material 16 subassembly. The first separator envelope 134 is next positioned between the spaced apart anodes 12, 14.

FIG. 7 illustrates anode pellet 12 supporting an outwardly extending anode lead 12A and anode pellet 14 supporting an outwardly extending anode lead 14A. Instead of the anodes 12, 14 having their own feedthrough, the anode leads 12A, 14A are connected to a feedthrough lead 138 extending through a conventional insulator and seal structure 140. The insulator and seal structure 140 can be a hermetic glass-to-metal-seal or, alternately, one similar to that described previously with respect to FIGS. 1 to 3 where the seal member 80 and 94 are not glass, but, instead, are a synthetic polymeric material such as an elastomeric material that is configured to seal between feedthrough lead 138 and the inner surface of a ferrule 142 for the feedthrough 140. A suitable polymeric material is, for example Master-Sil 151 made by Master Bond. While such a seal structure using only a synthetic polymeric material is not necessarily hermetic, acceptable isolation of the electrolyte from inside the casing 18 to the outside thereof is provided.

The anodes 12, 14/cathode active material 16 subassembly is then housed or contained inside a second separator envelope 144 comprising eleventh and twelfth separator sheets 146 and 148. The eleventh separator sheet 146 partially surrounds the anodes 12, 14 and cathode active material 16 housed in the first separator envelope 134 and comprises an outwardly extending peripheral margin 146A. A twelfth separator 148 has a size and shape configured to serve as a "lid" to the eleventh sheet 146. In that manner, the eleventh and twelfth separator sheets 146, 148 are joined to each other at coincident margins 146A, 148A by a heat seal or adhesive 150.

As shown, the anode leads 12A, 14A and the attached feedthrough lead 138 extend through a sidewall of the eleventh sheet 146. An adhesive 152 seals this opening. The insulator and seal structure 140 resides outside the second envelope 134. Moreover, the tab 34A for the cathode current collector 34 extends through a second opening in the eleventh separator sheet 146. This opening is also sealed with an adhesive 154. As depicted by arrows 156, before being positioned inside the casing 18, the coincident margins 146A, 148A are folded against the main body of the eleventh sheet 146.

It should be understood that the capacitor 10 of the present invention including the various bag-in-a-bag separator designs shown in FIGS. 5 to 7 are not limited to dual anode designs. Instead, the capacitor may comprise additional anodes and cathode current collectors including cathode active material on the current collector faces thereof. Moreover, while not shown in the drawings, a molded polymeric cradle or restraint is preferably provided for containing the anodes 12, 14 in the desired position should the capacitor 10 experience high shock and vibration conditions. Suitable restraints are described in U.S. Pat. No. 7,085,126 to Muffoletto et al. and U.S. Pat. No. 7,092,242 to Gloss et al., which are assigned to the assignee of the present invention and incorporated herein by reference.

Although several embodiments of the invention have been described in detail, for purposes of illustration, various modifications of each may be made without departing from the spirit and scope of the invention. Accordingly, the invention is not to be limited, except as by the appended claims.

What is claimed is:
1. A capacitor, comprising:
a) a casing;
b) a first anode of a first anode active material and a second anode of a second anode active material, wherein the first and second anodes are housed inside the casing;
c) a cathode comprising a cathode current collector having opposed first and second major faces supporting a first cathode active material thereon;
d) a first separator envelope housing the cathode inside the casing so that the first cathode active material resides between and is aligned with the first and second anodes;
e) a second separator envelope inside the casing, the second separator envelope housing the first and second anodes and the intermediate first separator envelope housing the cathode; and
f) an electrolyte contacting the cathode and the first and second anodes.

2. The capacitor of claim 1, wherein the cathode further comprises second and third cathode active materials supported by and in contact with a respective one of a first inner surface of the casing and a second inner surface of the casing, and wherein the second and third cathode active materials are aligned with an adjacent major face of the respective first and second anodes.

3. The capacitor of claim 1, wherein the second separator envelope is comprised of a second separator sheet having a second peripheral margin and a third separator sheet having a third peripheral margin, the second peripheral margin being secured to the third peripheral margin to thereby house the first separator envelope in the second separator envelope, the first separator envelope housing the cathode and residing between the first and second anodes.

4. The capacitor of claim 1, wherein the first anode is electrically connected in parallel to the second anode inside the casing.

5. The capacitor of claim 4, wherein an anode lead is electrically connected to the parallel connected first and second anodes, the anode lead extending outside the casing and being electrically isolated there from by an insulative seal.

6. The capacitor of claim 5, wherein the insulative seal is a hermetic seal comprising a sealing glass.

7. The capacitor of claim 5, wherein the insulative seal comprises a polymeric sealing material contacting the anode lead and a ferrule supported by the casing, the insulative seal being devoid of a hermetic sealing glass.

8. The capacitor of claim 1, wherein the first and second anode active materials are the same or different.

9. The capacitor of claim 8, wherein the first, second and third cathode active materials comprise ruthenium oxide.

10. The capacitor of claim 1, wherein the first and second anodes are sintered tantalum pellets that are characterized as having been anodized to a formation voltage that is greater than zero up to 550 V.

11. The capacitor of claim 1, wherein the first anode is electrically connected in parallel to the second anode outside the casing.

12. A capacitor, comprising:
a) a casing comprising first and second casing members secured to each other;
b) a first anode of a first anode active material and a second anode of a second anode active material, wherein the first and second anodes are housed inside the casing;
c) a cathode comprising a cathode current collector having opposed first and second major faces supporting a first cathode active material thereon;
d) a first separator envelope housing the cathode inside the casing so that the first cathode active material resides between and is aligned with the first and second anodes, the first separator envelope comprising first and second separator sheets having respective first and second peripheral margins that are secured to the cathode current collector, spaced from the cathode active material;

e) a second separator envelope comprising third and fourth separator sheets having respective third and fourth peripheral margins secured to the respective first and second separator sheets to thereby house the first and second anodes and the intermediate first separator envelope housing the cathode;

f) an anode lead electrically connected to the first and second anodes, the anode lead extending outside the casing and being isolated from the casing by an insulative seal; and g) an electrolyte contacting the cathode and the first and second anodes.

13. The capacitor of claim 12, wherein the cathode current collector comprises a tab that is secured to the casing serving as a terminal for the cathode.

14. The capacitor of claim 12, wherein the cathode further comprises second and third cathode active materials supported by and in contact with a respective one of a first inner surface of the casing and a second inner surface of the casing, and wherein the second and third cathode active materials are aligned with an adjacent major face of a respective one of the first and second anodes housed in the second separator envelope.

15. The capacitor of claim 12, wherein the insulative seal is a hermetic seal comprising a sealing glass.

16. The capacitor of claim 12, wherein the insulative seal comprises a polymeric sealing material contacting the anode lead and a ferrule supported by the casing, the insulative seal being devoid of a hermetic sealing glass.

17. The capacitor of claim 12, wherein the first and second anodes comprise tantalum, and wherein the first, second and third cathode active materials comprise ruthenium oxide.

18. The capacitor of claim 12, wherein the third and fourth peripheral margins of the third and fourth separator sheets are secured to the first and second peripheral margins of the respective first and second separator sheets.

19. A capacitor, comprising:
a) a casing;
b) a first anode of a first anode active material and a second anode of a second anode active material, wherein the first and second anodes are electrically connected in parallel inside the casing;
c) a feedthrough supported by the casing, wherein the feedthrough comprises an anode lead that is electrically isolated from the casing by an insulative seal, the anode lead being electrically connected to the parallel connected first and second anodes;
d) a cathode comprising a cathode current collector having opposed first and second major faces supporting a first cathode active material thereon, wherein a tab for the cathode current collector is secured to the casing;
e) a first separator envelope housing the cathode inside the casing with the first cathode active material residing between and being aligned with the first and second anodes, wherein the cathode current collector tab extends outside the first separator envelope;
f) a second separator envelope inside the casing, the second separator envelope housing the first and second anodes and the intermediate first separator envelope housing the cathode, wherein the current collector tab extends outwardly through a first opening in the second separator envelope, and the anode lead extends outwardly through a second opening in the second separator envelope; and
g) an electrolyte contacting the cathode and the first and second anodes.

20. The capacitor of claim 19, wherein the insulative seal is a hermetic seal comprising a sealing glass.

21. The capacitor of claim 19, wherein the insulative seal comprises a polymeric sealing material contacting the anode lead and a ferrule supported by the casing, the insulative seal being devoid of a hermetic sealing glass.

* * * * *